United States Patent
Richey, II

(10) Patent No.: US 6,990,980 B2
(45) Date of Patent: Jan. 31, 2006

(54) CARBON DIOXIDE-BASED BI-LEVEL CPAP CONTROL

(75) Inventor: Joseph B. Richey, II, Chagrin Falls, OH (US)

(73) Assignee: Invacare Corporation, Elyria, OH (US)

(*) Notice: Subject to any disclaimer, the term of this patent is extended or adjusted under 35 U.S.C. 154(b) by 393 days.

(21) Appl. No.: 09/967,274

(22) Filed: Sep. 27, 2001

(65) Prior Publication Data
US 2002/0104536 A1 Aug. 8, 2002

Related U.S. Application Data

(60) Provisional application No. 60/236,123, filed on Sep. 28, 2000.

(51) Int. Cl.
*A61M 16/00* (2006.01)

(52) U.S. Cl. .............. 128/204.26; 128/204.18; 128/204.23; 128/205.11

(58) Field of Classification Search ........ 128/204.23, 128/204.22, 204.18, 205.28, 204.26, 205.11, 128/204.21, 204.24
See application file for complete search history.

(56) References Cited

U.S. PATENT DOCUMENTS

| | | | |
|---|---|---|---|
| 3,921,628 A * | 11/1975 | Smythe et al. ........ | 128/204.21 |
| 4,011,859 A | 3/1977 | Frankenberger | |
| 4,121,578 A * | 10/1978 | Torzala ................. | 128/204.23 |
| 4,350,166 A | 9/1982 | Mobarry | |
| 4,506,678 A | 3/1985 | Russell et al. | |
| 4,648,396 A | 3/1987 | Raemer | |
| 4,651,729 A * | 3/1987 | Rae ...................... | 128/203.14 |
| 4,655,213 A | 4/1987 | Rapoport et al. | |
| 4,713,558 A | 12/1987 | Russell et al. | |
| 4,728,499 A | 3/1988 | Fehder | |
| 4,817,013 A | 3/1989 | Corenman et al. | |
| 4,944,310 A | 7/1990 | Sullivan | |
| 4,994,117 A | 2/1991 | Fehder | |
| 5,044,362 A * | 9/1991 | Younes ................. | 128/204.21 |
| 5,065,756 A | 11/1991 | Rapoport | |
| 5,117,819 A | 6/1992 | Servidio et al. | |
| 5,124,129 A | 6/1992 | Riccitelli et al. | |
| 5,134,995 A | 8/1992 | Gruenke et al. | |
| 5,148,802 A | 9/1992 | Sanders et al. | |
| 5,166,075 A | 11/1992 | Fehder | |
| 5,179,002 A | 1/1993 | Fehder | |
| 5,199,424 A | 4/1993 | Sullivan et al. | |
| 5,203,343 A | 4/1993 | Axe et al. | |
| 5,239,995 A | 8/1993 | Estes et al. | |
| 5,245,995 A | 9/1993 | Sullivan et al. | |
| 5,251,632 A * | 10/1993 | Delpy .................... | 600/323 |
| 5,279,289 A | 1/1994 | Kirk | |
| 5,313,937 A | 5/1994 | Zdrojkowski | |
| 5,335,650 A * | 8/1994 | Shaffer et al. ......... | 128/200.24 |
| 5,335,654 A | 8/1994 | Rapoport | |
| 5,343,878 A | 9/1994 | Scarberry et al. | |

(Continued)

*Primary Examiner*—Glenn K. Dawson
*Assistant Examiner*—Darwin P Erezo
(74) *Attorney, Agent, or Firm*—Calfee, Halter & Griswold LLP

(57) ABSTRACT

A system and method of providing bi-level CPAP therapy is provided that incorporates an infrared carbon-dioxide sensor to determine whether a patient is inhaling or exhaling. Patient exhalation causes the infrared light to be absorbed, while patient inhalation reduces the presence of carbon-dioxide causes little or no absorption of carbon-dioxide. The level of carbon-dioxide in an associated patient breathing interface is monitored for thresholds that trigger higher CPAP pressure upon inhalation and lower CPAP pressure upon exhalation.

33 Claims, 8 Drawing Sheets

U.S. PATENT DOCUMENTS

| | | |
|---|---|---|
| 5,353,788 A | 10/1994 | Miles |
| 5,394,882 A | 3/1995 | Mawhinney |
| 5,433,193 A | 7/1995 | Sanders et al. |
| 5,438,980 A | 8/1995 | Phillips |
| 5,445,160 A | 8/1995 | Culver et al. |
| 5,456,249 A | 10/1995 | Kirk |
| 5,458,137 A | 10/1995 | Axe et al. |
| 5,490,502 A | 2/1996 | Rapoport et al. |
| 5,492,113 A | 2/1996 | Estes et al. |
| 5,503,146 A | 4/1996 | Froehlich et al. |
| 5,522,382 A | 6/1996 | Sullivan et al. |
| RE35,295 E | 7/1996 | Estes et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,546,933 A | 8/1996 | Rapoport et al. |
| 5,549,106 A | 8/1996 | Gruenke et al. |
| 5,551,418 A | 9/1996 | Estes et al. |
| 5,551,419 A | 9/1996 | Froehlich et al. |
| 5,558,638 A | 9/1996 | Evers et al. |
| RE35,339 E | 10/1996 | Rapoport |
| 5,592,938 A | 1/1997 | Scarberry et al. |
| 5,598,838 A | 2/1997 | Servidio et al. |
| 5,630,411 A | 5/1997 | Holscher |
| 5,632,269 A | 5/1997 | Zdrojkowski |
| 5,655,522 A | 8/1997 | Mechlenburg et al. |
| 5,679,884 A | 10/1997 | Kirk |
| 5,682,878 A | 11/1997 | Ogden |
| 5,694,923 A | 12/1997 | Hete et al. |
| 5,701,883 A | 12/1997 | Hete et al. |
| 5,704,345 A | 1/1998 | Berthon-Jones |
| 5,715,812 A | 2/1998 | Deighan et al. |
| 5,738,106 A | 4/1998 | Yamamori et al. |
| 5,740,795 A | 4/1998 | Brydon |
| 5,765,563 A | 6/1998 | Vander Schaaf |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,845,636 A | 12/1998 | Gruenke et al. |
| 5,865,173 A | 2/1999 | Froehlich |
| 5,881,717 A | 3/1999 | Isaza |
| 5,881,723 A | 3/1999 | Wallace et al. |
| 5,901,704 A | 5/1999 | Estes et al. |
| 5,904,141 A | 5/1999 | Estes et al. |
| 5,915,379 A | 6/1999 | Wallace et al. |
| 5,915,380 A | 6/1999 | Wallace et al. |
| 5,927,274 A | 7/1999 | Servidio et al. |
| 5,937,851 A | 8/1999 | Serowski et al. |
| 5,947,115 A | 9/1999 | Lordo et al. |
| 5,953,713 A | 9/1999 | Behbehani et al. |
| 5,970,975 A | 10/1999 | Estes et al. |
| 6,017,315 A | 1/2000 | Starr et al. |
| 6,024,089 A | 2/2000 | Wallace et al. |
| 6,026,312 A | 2/2000 | Shemwell et al. |
| 6,029,660 A | 2/2000 | Calluaud et al. |
| 6,029,664 A | 2/2000 | Zdrojkowski et al. |
| 6,029,665 A | 2/2000 | Berthon-Jones |
| 6,044,843 A | 4/2000 | O'Neil et al. |
| 6,071,237 A * | 6/2000 | Weil et al. .................. 600/309 |
| 6,085,747 A | 7/2000 | Axe et al. |
| 6,091,973 A | 7/2000 | Colla et al. |
| 6,095,974 A | 8/2000 | Shemwell et al. |
| 6,102,042 A | 8/2000 | Hete et al. |
| 6,105,575 A | 8/2000 | Estes et al. |
| 6,123,074 A | 9/2000 | Hete et al. |
| 6,123,075 A | 9/2000 | Kirk |
| 6,135,106 A | 10/2000 | Dirks et al. |
| 6,138,675 A | 10/2000 | Berthon-Jones |
| 6,142,952 A | 11/2000 | Behbehani et al. |
| 6,152,129 A | 11/2000 | Berthon-Jones |
| 6,155,257 A * | 12/2000 | Lurie et al. ............ 128/204.23 |
| 6,155,986 A | 12/2000 | Brydon et al. |
| 6,182,657 B1 | 2/2001 | Brydon et al. |
| 6,183,423 B1 | 2/2001 | Gaumond et al. |
| 6,212,435 B1 | 4/2001 | Lattner et al. |
| 6,213,119 B1 | 4/2001 | Brydon et al. |
| 6,237,592 B1 | 5/2001 | Surjadi et al. |
| 6,237,593 B1 | 5/2001 | Brydon |
| 6,240,921 B1 | 6/2001 | Brydon et al. |
| 6,253,764 B1 | 7/2001 | Calluaud |
| 6,257,234 B1 | 7/2001 | Sun |
| 6,269,811 B1 | 8/2001 | Duff et al. |
| 6,269,812 B1 | 8/2001 | Wallace et al. |
| 6,279,569 B1 | 8/2001 | Berthon-Jones |
| 6,299,581 B1 | 10/2001 | Rapoport et al. |
| 6,302,105 B1 | 10/2001 | Wickham et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,796,305 B1 * | 9/2004 | Banner et al. ......... 128/204.21 |
| 2001/0004894 A1 | 6/2001 | Bourdon |
| 2001/0015204 A1 | 8/2001 | Hansen et al. |
| 2001/0027791 A1 | 10/2001 | Wallace et al. |
| 2001/0027792 A1 | 10/2001 | Berthon-Jones et al. |
| 2001/0035186 A1 | 11/2001 | Hill |

\* cited by examiner

CARBON DIOXIDE-BASED BI-LEVEL CPAP CONTROL

CROSS-REFERENCE TO RELATED APPLICATIONS

This patent application is related to provisional application Ser. No. 60/236,123, filed Sep. 28, 2000 titled "Carbon Dioxide-Based Bi-Level CPAP Control," which is hereby fully incorporated by reference.

FIELD OF THE INVENTION

The invention relates generally to the administration of constant positive airway pressure (CPAP) to treat obstructive sleep apnea, and more particularly, to methods and apparatuses for administering a higher CPAP upon inhalation and a lower CPAP upon exhalation.

BACKGROUND OF THE INVENTION

Obstructive sleep apnea is an airway breathing disorder caused by relaxation of the muscles of the upper airway to the point where the upper airway collapses or becomes obstructed by these same muscles. It is known that obstructive sleep apnea can be treated through the application of pressurized air to the nasal passages of a patient. The application of pressurized air forms a pneumatic splint in the upper airway of the patient thereby preventing the collapse or obstruction thereof.

Within the treatment of obstructive sleep apnea, there are several known CPAP regimens including, for example, mono-level CPAP and bi-level CPAP. Mono-level CPAP involves the constant application of a single therapeutic CPAP level. That is, through the entire breathing cycle, a single therapeutic positive air pressure is delivered to the patient. While such a regimen is successful in treating obstructive sleep apnea, some patients experience discomfort when exhaling because of the level of positive air pressure being delivered to their airways during exhalation.

In response to this discomfort, bi-level CPAP regimens were developed. Bi-level CPAP involves delivering a higher therapeutic CPAP during inhalation and a lower therapeutic CPAP during exhalation. The higher therapeutic CPAP level is commonly known as inspiratory positive airway pressure or "IPAP." The lower therapeutic CPAP level is commonly known as expiratory positive airway pressure or "EPAP." Since the EPAP is lower than the IPAP, the patient needs to do less work during exhalation to exhale and thus experiences less discomfort, compared to the mono-level CPAP regimen.

However, the development of bi-level CPAP significantly increased the sophistication of CPAP devices because the devices must accurately determine when the patient is inhaling and exhaling and to properly coordinate the IPAP and EPAP levels thereto. One approach is to determine the instantaneous and average flow rates of air being delivered to the patient and then to compare the two to determine whether a patient was inhaling or exhaling. If the instantaneous flow rate is greater than the average flow rate, the patient is deemed to be inhaling. If the instantaneous flow rate is less than the average flow rate, the patient is deemed to be exhaling. However, using the instantaneous and average flow rates of the air being delivered to the patient has several disadvantages including accuracy and response time. In this regard, the flow of air is generally turbulent and therefore difficult to measure accurately. Additionally, leakages caused by loose fitting patient breathing interfaces such as, for example, nasal and mouth masks, contribute to the difficulty of determining accurate air flow rates. Closely connected thereto, the turbulent flow and difficulty of accurate measurement necessarily cause a slow response time in changing between IPAP and EPAP levels. Hence, a bi-level CPAP device that does not suffer from these deficiencies is highly desirable.

SUMMARY OF THE INVENTION

According to one embodiment of the present invention, a carbon-dioxide sensor is used to determine whether a patient undergoing bi-level CPAP treatment for obstructive sleep apnea is inhaling or exhaling. The carbon-dioxide sensor uses infrared light to determine the presence or absence of carbon-dioxide in a patient breathing interface such as, for example, a nasal and mouth mask, worn by the patient. In this regard, the carbon-dioxide sensor includes, for example, an infrared light emitter and detector separated by an air gap. Patient exhalation results in carbon-dioxide being present in the air gap. This causes less infrared light to be transmitted to the detector due to the carbon-dioxide absorbing a portion of the infrared light. Conversely, patient inhalation results in little or no carbon-dioxide being present in the air gap. This causes more infrared light to be transmitted to the detector because there is little or no carbon-dioxide present to absorb the infrared light. Through such detection, the logic of the present invention coordinates the IPAP and EPAP levels to provide the patient with a comfortable bi-level CPAP regimen.

In a first embodiment, the level of carbon-dioxide is monitored to determine whether it is above or below a threshold parameter or value. If the level of carbon dioxide is above the threshold, the patient is exhaling and an EPAP level is provided. If the level of carbon-dioxide is below the threshold, the patient is inhaling and an IPAP level is provided to the patient. Hence, the same threshold is used once to trigger EPAP and again to trigger IPAP.

In a second embodiment, monostable timer control is used to trigger the EPAP and IPAP. In this regard, the monostable timer is trigger to its fixed duration on state when the level of carbon-dioxide is decreasing and falls below a threshold parameter or value. Once this happens, the patient is inhaling and an IPAP level is provided. Upon expiration of the monostable timer's fixed duration on state, patient exhalation is assumed and an EPAP level is provided until the monostable timer is once again triggered.

It is therefore an object of the present invention to provide a system and method of providing a higher positive airway pressure breathing gas during patient inhalation and a lower positive airway pressure breathing gas during patient exhalation.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

DETAILED DESCRIPTION OF ILLUSTRATED EMBODIMENT

Figure 1:
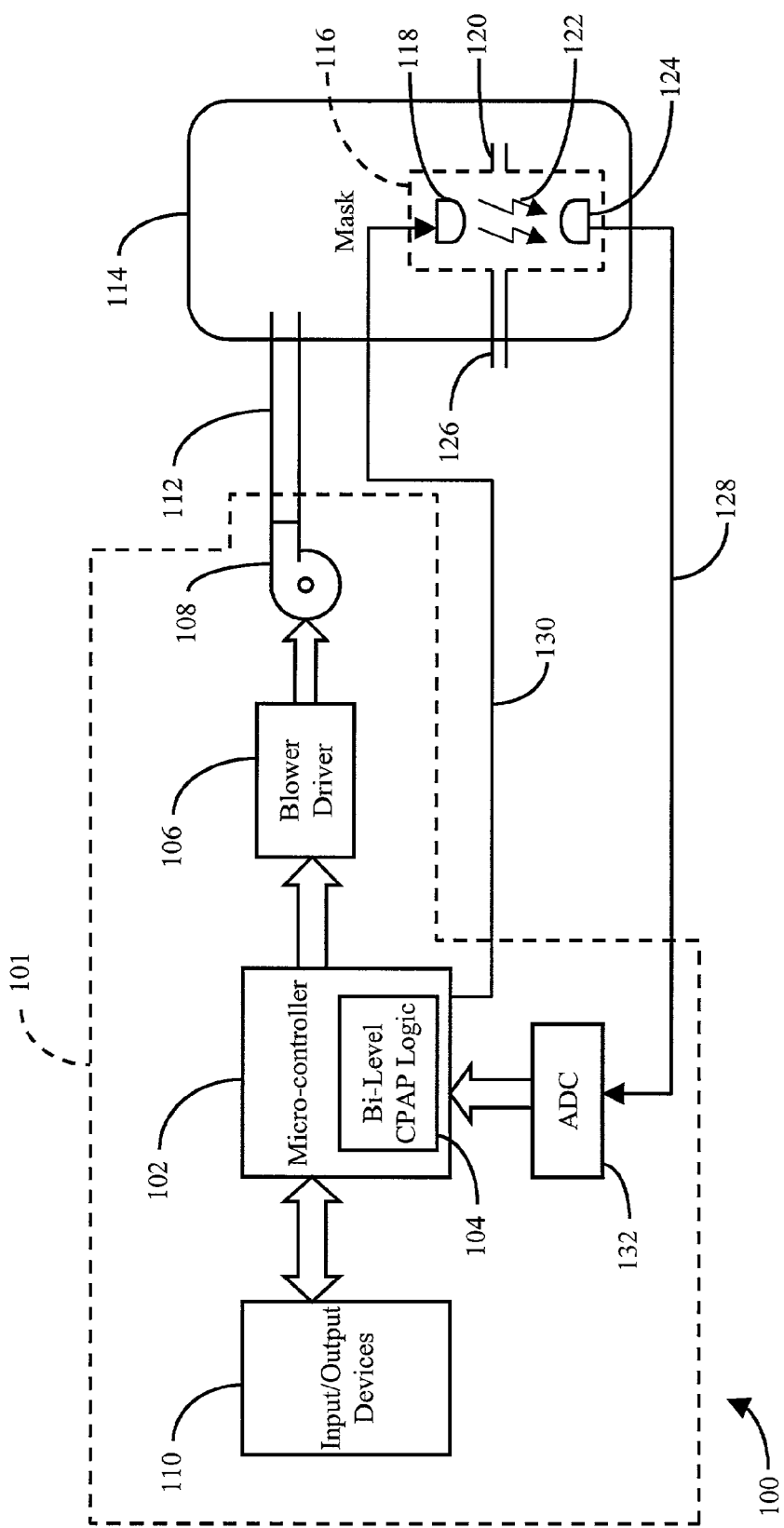
FIG. 1 is a functional block diagram of a system of the present invention having a carbon-dioxide sensor integral with a nasal mask.

Illustrated in FIG. 1 is a first bi-level CPAP system 100 of the present invention. The system has a bi-level CPAP apparatus 101 and a patient breathing interface 114. The bi-level CPAP apparatus 101 has a micro-controller 102 with associated bi-level CPAP logic 104. The micro-controller 102 interfaces with a plurality of components including input/output devices 110, analog-to-digital converter (ADC) 132, and blower driver 106. Input/Output devices 110 include, for example, controls that allow a clinician or doctor to set the IPAP and EPAP levels in micro-controller 102 and in bi-level CPAP logic 104. Blower driver 106 interfaces with and drives blower 108 through a range of variable speeds that result in a range of variable air pressures that define the IPAP and EPAP levels. The blower 108 preferably has a motor and a fan and is driven by a pulse-width modulated (PWM) signal wherein the pulse width or duty cycle defines the variable speed and pressure of the blower. Alternatively, an adjustable valve can be used to vary the bi-level CPAP pressure between IPAP and CPAP levels such as described in U.S. Pat. No. 5,433,193, which is hereby fully incorporated by reference.

System 100 also includes a patient breathing interface 114, such as a mask, that is worn by a patient that is to receive bi-level CPAP therapy. Patient breathing interface 114 is connected to blower 108 through supply tubing 112, which supplies the IPAP and EPAP levels to the patient from the CPAP apparatus 101. In the present embodiment, patient breathing interface 114 has a carbon-dioxide sensor 116 integral therewith for detecting the presence of carbon-dioxide in the mask.

Carbon-dioxide sensor 116 preferably includes an infrared light emitter 118 and an infrared light detector 124. Infrared light emitter 118 is preferably an incandescent light source emitting light in the infrared frequency range. However, infrared light emitting diodes can also be employed. Infrared light detector 124 is of conventional design. Infrared light emitter 118 is separated from infrared light detector 124 by an air gap such that infrared light 122 emitted from emitter 118 is directed across the air gap and towards detector 124.

In this regard, it is known that carbon-dioxide absorbs light in the infrared energy spectrum. See, for example, U.S. Pat. No. 4,648,396 to Raemer, which is hereby fully incorporated by reference. Hence, when a gas having carbon-dioxide is present in the air gap between infrared light emitter 118 and detector 124, less infrared light is transmitted to detector 124 than if no carbon-dioxide was present in the air gap. This is indicated by the output (i.e., signal 128) of detector 124 falling to a level indicative of the amount of infrared light that is not being absorbed by the carbon-dioxide. In this manner, carbon-dioxide sensor 116 senses the amount of carbon-dioxide present.

Carbon-dioxide sensor 116 further includes an input port 120 and in output port 126. Input port 120 allows gases present in patient breathing interface 114 to pass into carbon-dioxide sensor 116 and between the air gap separating infrared light emitter 118 and detector 124 for carbon-dioxide detection. Output port 126 allows venting of the gases in carbon-dioxide sensor 116 to the outside atmosphere. Configured as such, carbon-dioxide sensor 116 also performs a venting function provided for by most conventional patient breathing interfaces.

As shown in FIG. 1, bi-level CPAP apparatus 101 is in circuit communication with infrared light emitter 118 and detector 124. More particularly, micro-controller 102 drives infrared light emitter 118 on and off through signal line 130 and conventional drive circuitry (not shown) Micro-controller 102 also reads the output of infrared light detector 124 through signal line 128 and ADC 132. In this manner, micro-controller 102 controls carbon-dioxide sensor 116 and reads its output signal to thereby determine the presence or absence of carbon-dioxide in patient breathing interface 114. As will be described in more detail in connection with the logic of FIG. 4, the presence of carbon-dioxide indicates that a wearer of patient breathing interface 114 is exhaling and the absence of carbon-dioxide indicates that the wearer is inhaling. By knowing when the patient is inhaling and exhaling, micro-controller 102 and bi-level CPAP logic 104 can vary the air pressure delivered by blower 108 to the proper IPAP and EPAP levels set by the clinician or doctor.

Figure 2:
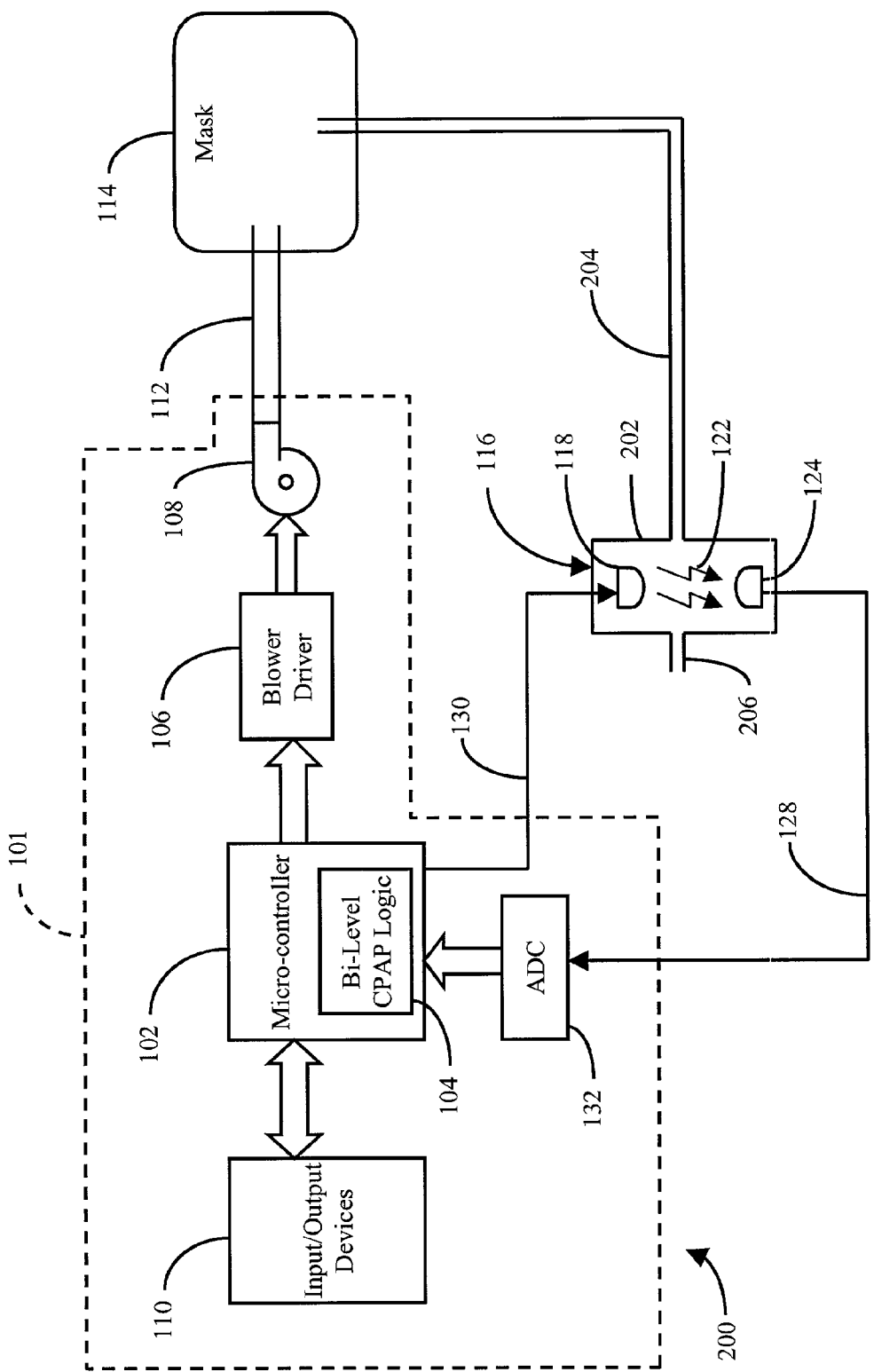
FIG. 2 is a functional block diagram of a system of the present invention having a carbon-dioxide sensor external to a nasal mask.

FIG. 2 illustrates a bi-level CPAP system 200 that is similar system 100 of FIG. 1, except that carbon-dioxide sensor 116 is external to the patient breathing interface 114. In system 200, carbon-dioxide sensor 116 has a housing 202 that is connected to patient breathing interface 114 through tubing 204. Tubing 204 functions as the input port to carbon-dioxide sensor 116 by delivering gases thereto from patient breathing interface 114. Housing 202 also includes an output port 206 that allows venting of the gases in carbon-dioxide sensor 116 to the outside atmosphere.

Figure 3:
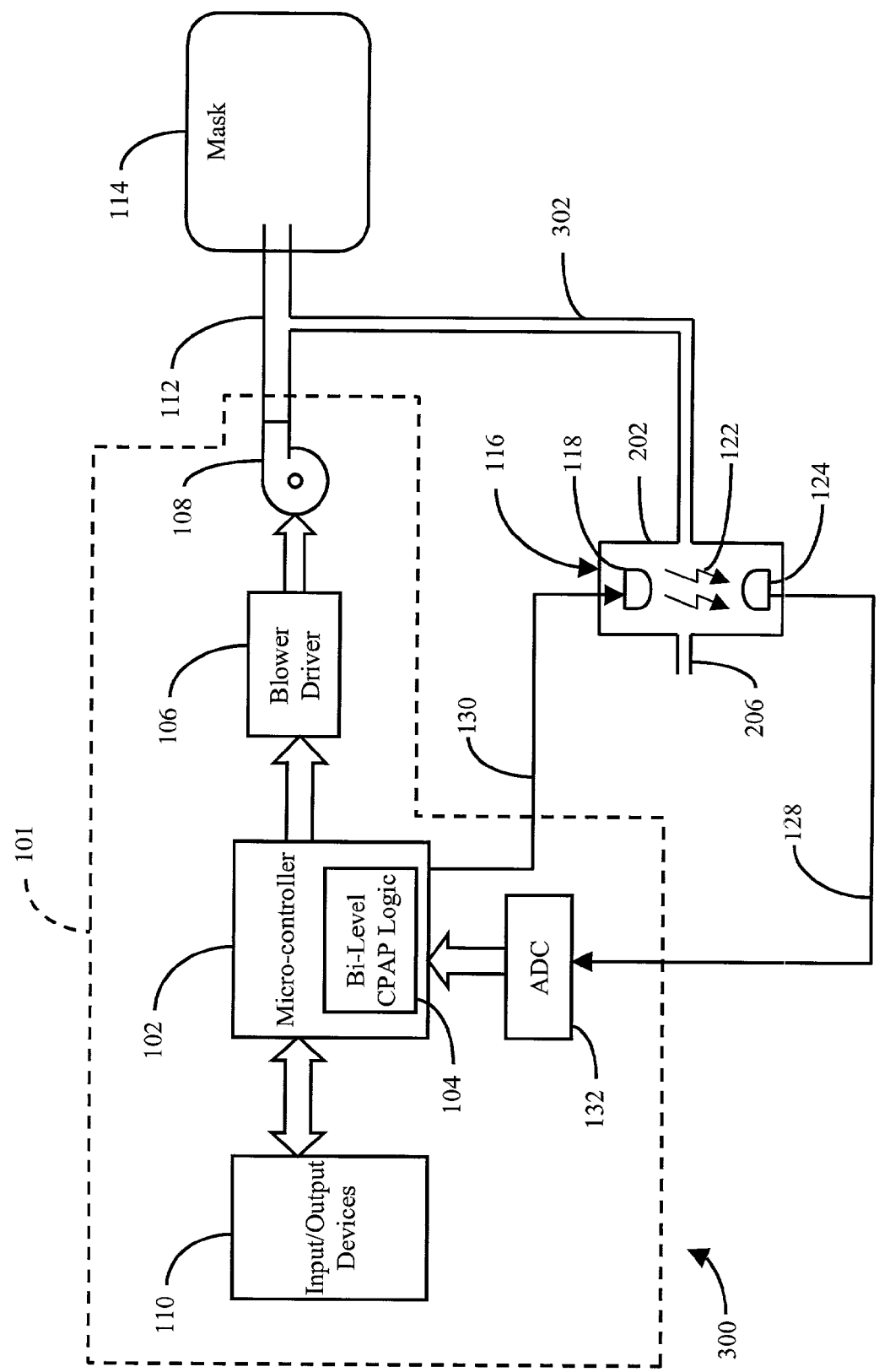
FIG. 3 is a functional block diagram of a system of the present invention having a carbon-dioxide sensor external to a nasal mask and indirectly connected thereto.

FIG. 3 illustrates a bi-level CPAP system 300 that is similar to system 200 of FIG. 2, except that carbon-dioxide sensor 116 is not directly connected to patient breathing interface 114. Rather, carbon-dioxide detector 116 is indirectly connected to patient breathing interface 114 via sensor tubing 302 and supply tubing 112. In all other aspects, systems 200 and 300 are similar to system 100 of FIG. 1.

Figure 4:
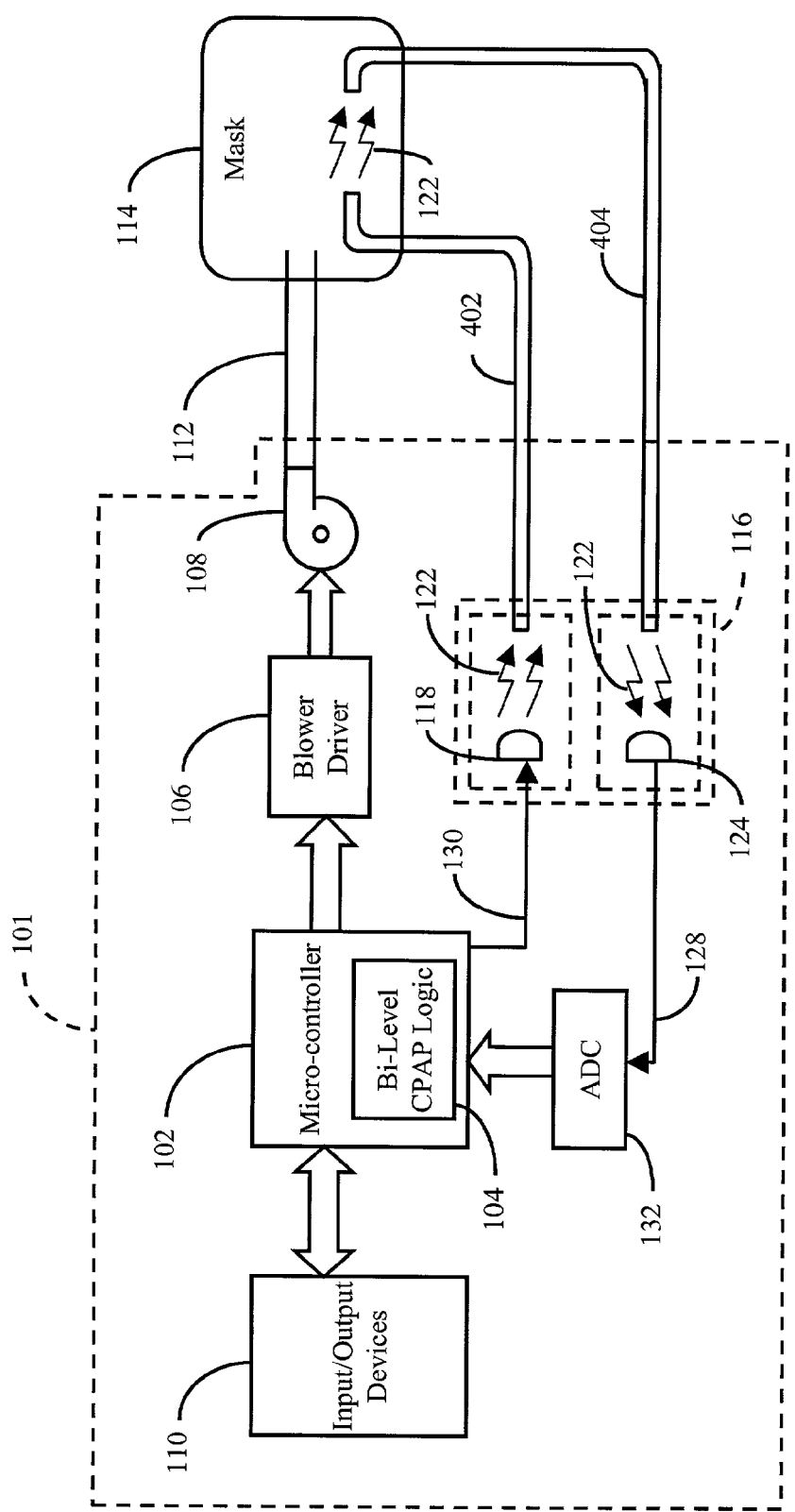
FIG. 4 is a functional block diagram of a system of the present invention having a carbon-dioxide sensor that is connected to a nasal mask with optical fibers.

Illustrated in FIG. 4 is a system 400 of the present invention that employs optical fibers to carry infrared light to and from patient breathing interface 114. In particular, carbon-dioxide sensor 116 is external to patient breathing interface 114 and preferably located within bi-level CPAP apparatus 101. A plurality of optical fibers carry infrared light from infrared light emitter 118 to patient breathing interface 114 and back to infrared light detector 124. Within patient breathing interface 114, optical fibers 402 and 404 are terminated such that infrared light exiting optical fiber 402 is ultimately directed across an air gap and to optical fiber 404 for return to infrared light detector 124. The fiber optic terminations and air gap are preferably disposed across one or more of the venting mechanisms (i.e., one or more holes or vents) of patient breathing interface 114. In this regard, exhaled gases that are normally vented through such mechanisms can be monitored by carbon-dioxide sensor 116. It should also be noted in FIG. 4 that optical fibers 402 and 404 can be connected in a similar manner to supply tube 112 rather patient breathing interface 114. Configured as such, system 400 is particularly advantageous because it does not require the use of additional tubing and allows the carbon-dioxide sensor 116 to be housed with bi-level CPAP apparatus 101.

Figure 5:
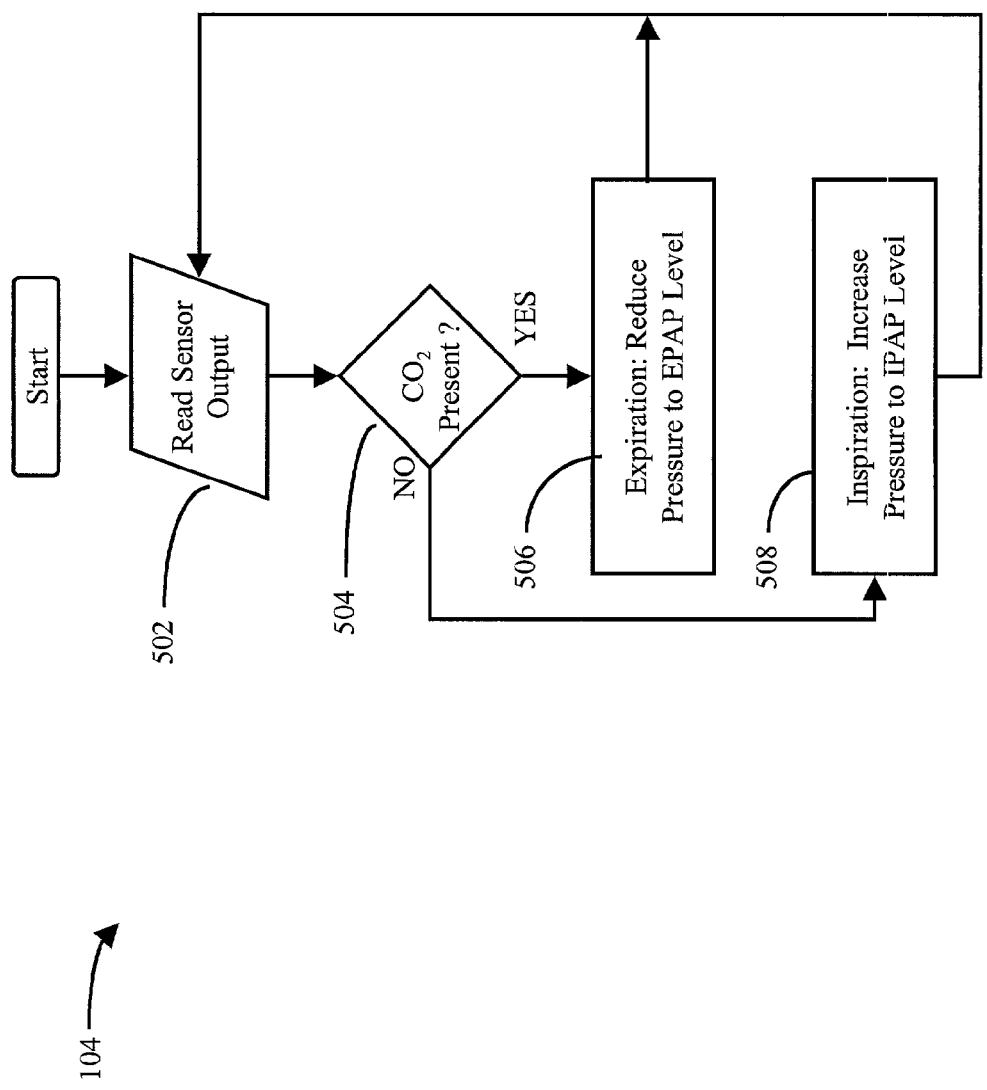
FIG. 5 is a flow chart of the bi-level CPAP logic of the present invention.

Referring now to FIG. 5, a flowchart illustrating the bi-level CPAP logic 104 of the present invention is shown. The bi-level CPAP logic 104 is executed by micro-controller 102. The logic starts in step 502 where micro-controller 102 reads the value of carbon-dioxide sensor 116 output signal 128.

In step 504, the logic determines if carbon-dioxide is present in the patient breathing interface by comparing the value of the sensor output signal 128 against a threshold parameter or value. The threshold parameter or value is preferably a carbon-dioxide level within the patient breathing interface that is representative of the state of exhalation by the patient. If the value of sensor output signal 128 is less than the threshold parameter, then carbon-dioxide is sufficiently present and, therefore, the patient is exhaling. In this scenario, the logic advances to step 506. In step 506, micro-controller 102 directs blower 108 to reduce its output pressure to EPAP level by preferably decreasing the duty cycle of the blower's PWM driving signal. After step 506, the logic loops back to step 502 and once again reads the value of carbon-dioxide sensor 116 output signal 128.

However, if in step 504 the value of sensor output signal 128 is greater than the threshold parameter, then carbon-dioxide is deemed to be sufficiently absent and, therefore, the patient is inhaling. In this scenario, the logic advances to step 508 where the micro-controller 102 directs blower 108 to increase its output pressure to IPAP level by preferably increasing the duty cycle of the blower's PWM driving signal. After step 508, the logic loops back to step 502 and once gain reads the carbon-dioxide sensor 116 output signal 128 to determine the appropriate CPAP level (i.e., IPAP or EPAP). In this manner, micro-controller 102 reads carbon-dioxide sensor 116 to determine the presence and absence of carbon-dioxide and to properly coordinate the IPAP and EPAP Levels with the patient's inspiratory and expiratory cycles.

Figure 6:
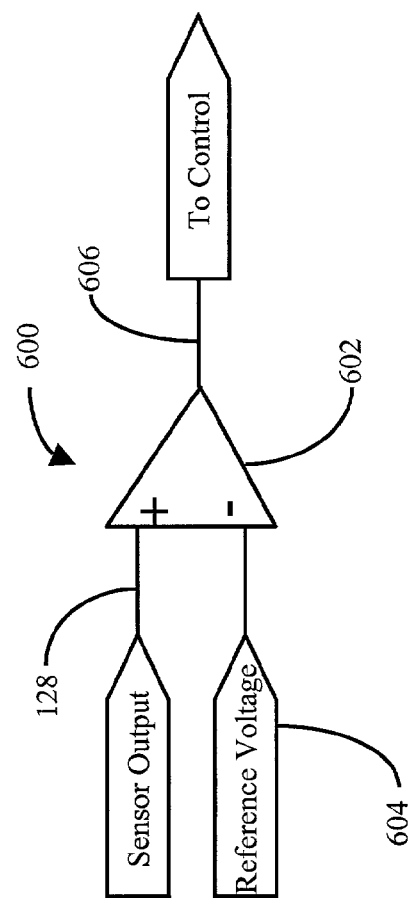
FIG. 6 is a schematic diagram of a comparator circuit of the present invention.

Referring now to FIG. 6, an analog comparator circuit 600 is shown that can be used as an alternative to ADC 132. The circuit 600 preferably includes an operational amplifier 602 that receives sensor output signal 128 at its positive input terminal and a reference or threshold voltage signal 604 at its negative input terminal. The output 606 of operational amplifier 602 is preferably connected to micro-controller 102 or other CPAP control circuitry.

Figure 7:
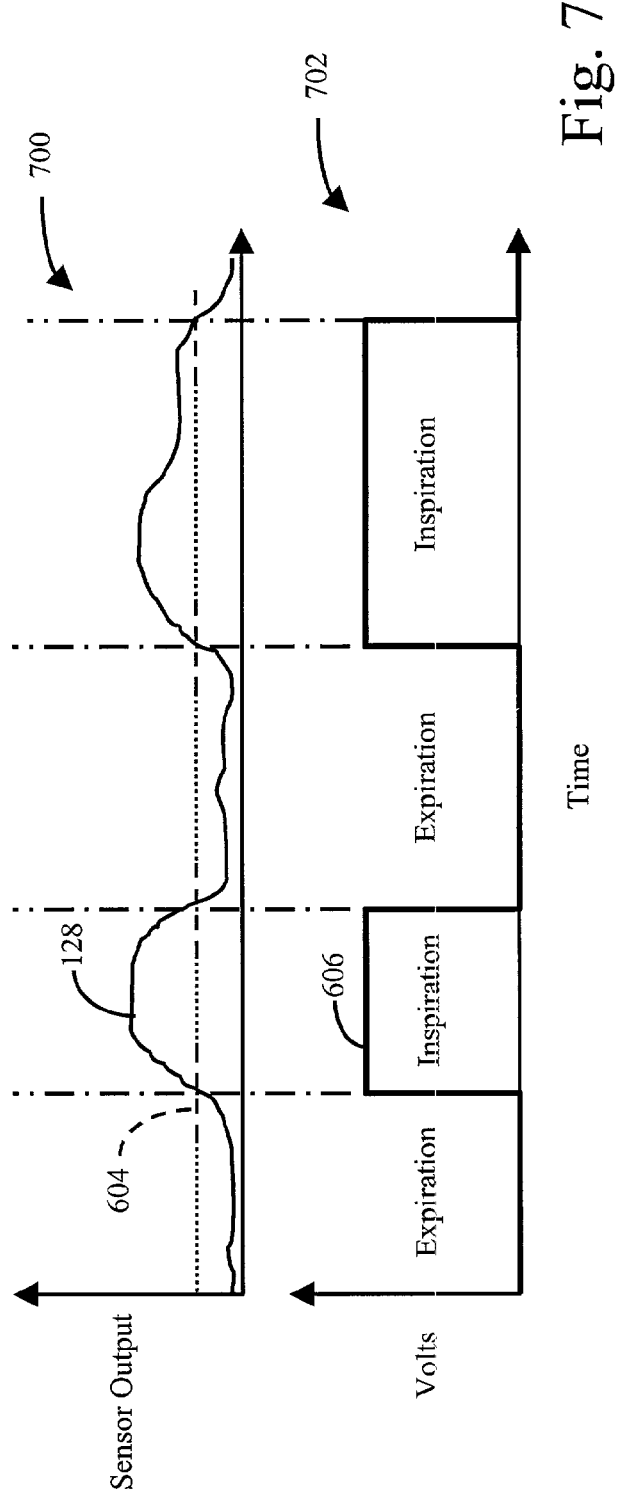
FIG. 7 illustrates graphs of the input and output signals of the comparator circuit of FIG. 5.

As shown in graphs 700 and 702 of FIG. 7, whenever sensor output signal 128 is greater than reference or threshold parameter, as represented by voltage signal 604, comparator 500 output signal 606 preferably increases to a positive voltage level. This indicates that carbon-dioxide is sufficiently absent so as to signify that the patient is inhaling and that blower 108 should provide the prescribed IPAP level. Whenever sensor output signal 128 is less than the reference or threshold parameter 604, comparator 600 output signal 606 preferably falls to a lower voltage level. This indicates that carbon-dioxide is sufficiently present so as to signify that the patient is exhaling and that blower 108 should provide the prescribed EPAP level. Alternately, threshold parameter 604 can be in the form of first and second threshold parameter: one for inhalation detection and one for exhalation detection. This configuration compensates for potential differences in carbon-dioxide inhalation and exhalation thresholds.

Figure 8:
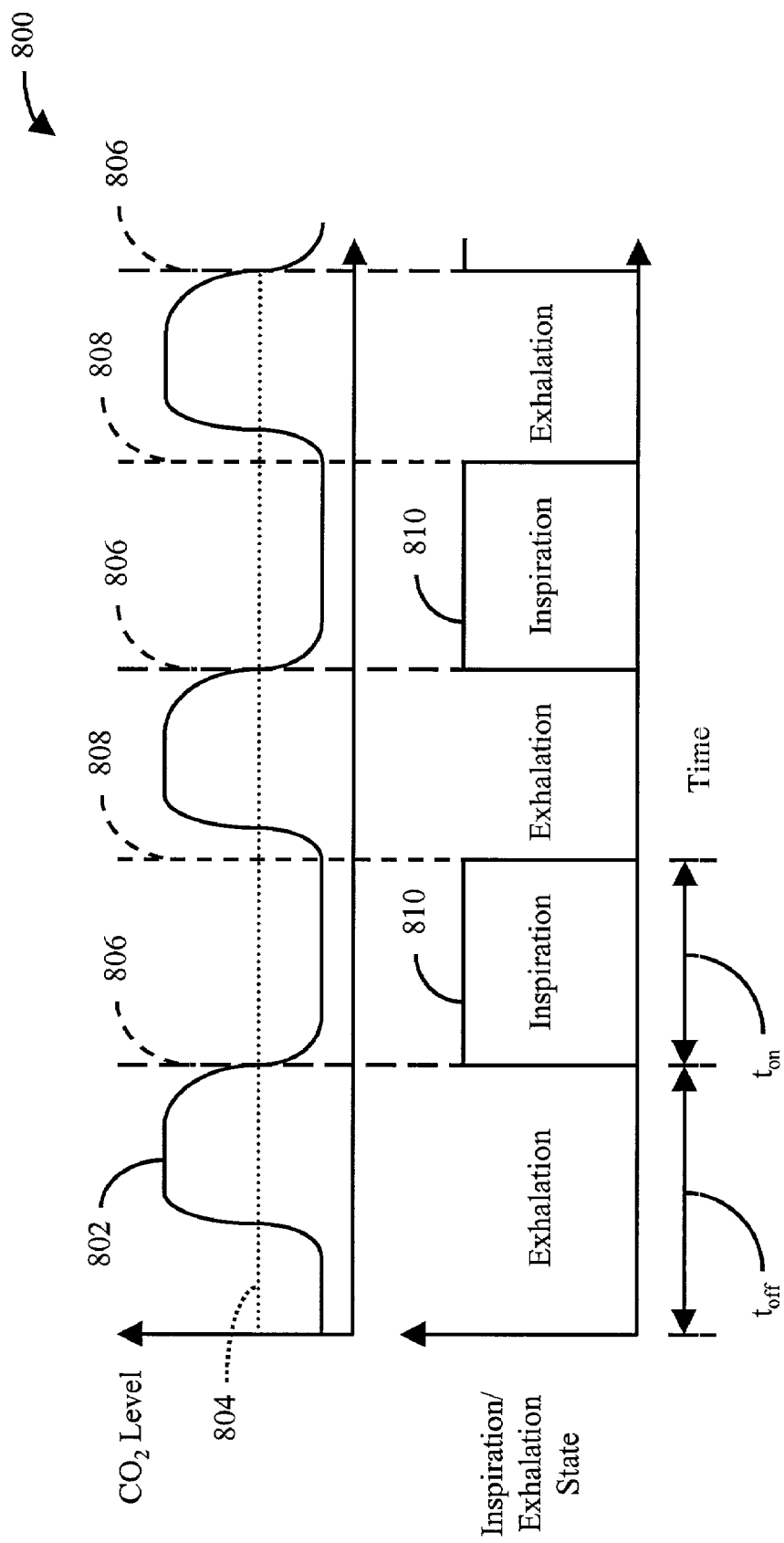
FIG. 8 illustrates a monostable timer control embodiment of the present invention.

Referring now to FIG. 8, a second embodiment of the present invention is illustrated that incorporates a monostable timer control to coordinate the IPAP and EPAP levels with the patient's breathing cycles. The monostable timer control can be implemented in any of the CPAP embodiments of FIGS. 1 through 4 wherein the monostable timer control is incorporated into bi-level CPAP logic 104.

In this regard, a monostable timer has one stable state and one quasi-stable state. For example, a timer having a variable off time and a fixed on time, or vice-versa, is generally known as a monostable timer. In the present embodiment, the variable off time of the monostable timer defines the exhalation state and the fixed on time defines the inhalation state. The opposite configuration can also be used. The monostable timer of the present invention also has a trigger in the form of a carbon-dioxide threshold level.

Referring now to FIG. 8 more particularly, the incorporation of a monostable timer control for governing the relationship between the level of carbon-dioxide associated with the patient breathing apparatus 114 and the inhalation and exhalation breathing states is generally illustrated at 800. In this regard, a representative carbon-dioxide level is shown over several patient breathing cycles is indicated by curve 802. As is commonly understood, more carbon-oxide is present in the patient breathing interface during exhalation than inhalation. Also illustrated is a threshold parameter 804 that serves to trigger the monostable timer of the present embodiment. Threshold parameter 804 is preferably defined as a carbon-dioxide level seen at the trailing or decreasing portion of the carbon-dioxide curve 802. The trigger points established by threshold parameter 804 are further illustrated by trigger lines 806. Hence, during patient exhalation, the level of carbon-dioxide increases over time to a certain level in the patient breathing interface or associated tubing. Venting by the patient breathing interface causes the carbon-dioxide level to begin decreasing. However, it is not until patient inhalation does the carbon-dioxide level decrease quickly over time so as to fall below threshold parameter 804 and trigger the monostable timer at 806.

In the present embodiment, during patient exhalation, the monostable timer is in its off state $t_{off}$ and micro-controller 102 directs blower 108 to provide an EPAP level to patient breathing interface 114. By providing an EPAP level, the patient can more comfortably exhale against a lower positive airway pressure. Once the carbon-dioxide level 802 rises and then falls below threshold parameter 804 to trigger the monostable timer at 806, the monostable timer changes to its on state $t_{on}$ for a fixed, predetermined time duration. This fixed, predetermined on time duration $t_{on}$ represents patient inhalation 810. The fixed, predetermined on time duration $t_{on}$ is based on the observation that during sleep most patient inhalation cycles have the same, or very nearly the same, duration. The monostable timer change of state from $t_{off}$ to $t_{on}$ causes micro-controller 102 to direct blower 108 to provide an IPAP level to the patient breathing interface 114 for the duration of time defined by $t_{on}$. By providing an IPAP level, a higher positive airway pressure is delivered to the patient during inhalation. Upon expiration of the time $t_{on}$, the monostable timer changes to its off state, as represented by lines 808. As described above, this causes micro-controller 102 to direct blower 108 to provide an EPAP level to the patient breathing interface 114 because the patient is about to exhale. The process is then repeated for the next patient breathing cycle.

Hence, the monostable timer control of the present invention provides a single trigger method for coordinating IPAP and EPAP levels with patient inhalation and exhalation. The trigger is defined by monitoring the carbon-dioxide level associated with the patient breathing interface for a falling level that crosses a predetermined threshold. The trigger defines a change in state of the monostable timer from an off state to an on state. The off state represents patient exhalation and causes the present invention to provide an EPAP level. The on state represents patient inhalation and causes the present invention to provide an IPAP level for a fixed, predetermined time duration. Upon expiration of the fixed, predetermined time duration, the present invention lowers the pressure back to EPAP level for patient exhalation. The process is repeated for each patient breathing cycle.

Figure 9:
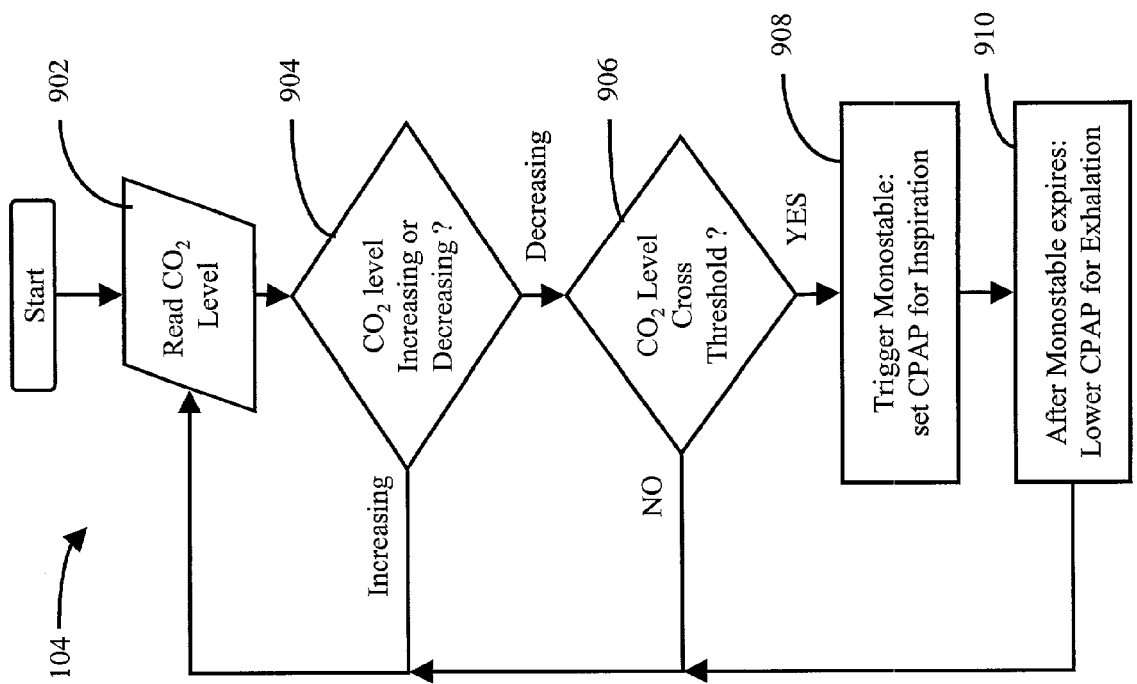
FIG. 9 is a flowchart of the monostable timer control logic of the present invention.

Referring now to FIG. 9, a flowchart illustrating the monostable timer control of bi-level CPAP logic 104 is shown. The logic commences in step 902 where the carbon-dioxide level associated with the patient breathing interface is sensed or monitored via carbon-dioxide sensor 116. Initially, the present invention provides an EPAP level until triggered. The logic then proceeds to step 904 where the sensed carbon-dioxide level is tested to determine whether it is increasing or decreasing. If the carbon-dioxide level is increasing, then the patient is exhaling and the EPAP level will continue to be provided. However, if the carbon-dioxide level is decreasing, the patient's breathing cycle is then starting a transition from exhalation to inhalation and the logic proceeds to step 906.

In step 906, the logic tests to determine whether the decreasing carbon-dioxide level has crossed a threshold parameter or value representing the state of patient inhalation. If the decreasing carbon-dioxide level has not crossed the threshold parameter, the logic loops back to step 902 to once again monitor the carbon-dioxide level. However, if the decreasing carbon-dioxide level has fallen to or below the threshold, then the logic advances to step 908 where the monostable timer is triggered to its on state. As described above, triggering the monostable timer causes an IPAP level to be delivered to the patient breathing interface for a fixed, predetermined time duration. Upon expiration of the fixed, predetermined time duration, the logic advances to step 910 where the monostable timer changes to its off state and an EPAP level is once again delivered to the patient breathing interface. After step 910, the logic loops back to step 902 and the process repeats. In this manner, a signal trigger is used to provide an IPAP level to a patient for a fixed, predetermined time duration for inhalation and an EPAP level to the patient for the duration of exhalation.

While the present invention has been illustrated by the description of embodiments thereof, and while the embodiments have been described in considerable detail, it is not the intention of application to restrict or in any way limit the scope of the appended claims to such detail. Additional advantages and modifications will readily appear to those skilled in the art. For example, the carbon-dioxide level can be quantitatively measured and used to raise or lower the IPAP or EPAP level in a step-wise fashion until obstructive sleep apnea no longer occurs. Still further, the carbon-dioxide sensor 116 of the present invention can be substituted with a temperature or humidity sensor. More specifically, exhalation and inhalation can be distinguished based on the temperature of the inhaled and exhaled gases. In this regard, exhaled gases have a higher temperature than inhaled gases and the temperature sensor would detect such a difference. Exhalation and inhalation can also be distinguished based on the water content or humidity level of the inhaled and exhaled gases. In this regard, exhaled gases have a higher humidity level than inhaled gases and the humidity sensor would detect such a difference. Still further, the present invention can be implemented with a microprocessor controlled system or discrete circuit element system. For example, a discrete circuit such as, for example, a Schmitt Trigger can be used to sense the carbon-dioxide level. Therefore, the invention, in its broader aspects, is not limited to the specific details, the representative apparatus, and illustrative examples shown and described. Accordingly, departures may be made from such details without departing from the spirit or scope of the applicant's general inventive concept.

What is claimed is:

1. A method of providing a breathing gas comprising the steps of:
sensing a carbon-dioxide level associated with a patient breathing interface;
determining if the level of carbon-dioxide is increasing or decreasing;
if the level is decreasing, determining if the level of carbon-dioxide has crossed a threshold parameter;
if the carbon-dioxide level has crossed the threshold parameter, increasing the breathing gas pressure provided to the patient breathing interface;
decreasing the breathing gas pressure provided to the patient breathing interface after a predetermined period of time; and
the increasing and decreasing of breathing gas pressure maintaining a positive pressure sufficient to sustain open the airway of a patient wearing the breathing interface.

2. The method of claim 1 wherein the step of sensing a carbon-dioxide level associated with a patient breathing interface comprises sensing the carbon-dioxide level using infrared light.

3. The method of claim 1 wherein the step of sensing a carbon-dioxide level associated with a patient breathing interface comprises emitting infrared light within the patient breathing interface.

4. The method of claim 3 wherein the step of sensing a carbon-dioxide level associated with a patient breathing interface comprises detecting infrared light within the patient breathing interface.

5. The method of claim 4 wherein the step of detecting infrared light comprising sensing the infrared light in a fiber optic cable coupled to the patient breathing interface.

6. The method of claim 3 wherein the step of emitting comprising emitting infrared light into a fiber optic cable connected to the patient breathing interface.

7. The method of claim 1 wherein the step of sensing a carbon-dioxide level associated with a patient breathing interface comprises sensing the carbon-dioxide level vented from the patient breathing interface.

8. The method of claim 1 further comprising the step of initiating a monostable timer if the carbon-dioxide level has crossed the threshold parameter.

9. The method of claim 8 wherein the step of decreasing the breathing gas pressure provided to the patient breathing interface after a predetermined period of time comprises decreasing the breathing gas pressure upon expiration of the monostable timer.

10. The method of claim 1 further comprising the step of initiating a timer if the carbon dioxide level has crossed the threshold parameter.

11. A method of providing a breathing gas to a patient comprising the steps of:

sensing a carbon-dioxide level associated with a patient breathing interface;
determining if the sensed level of carbon-dioxide is increasing or decreasing;
if the sensed carbon-dioxide level is increasing, determining if the sensed carbon-dioxide level has crossed a first threshold parameter;
if the sensed carbon-dioxide level has crossed the first threshold parameter, decreasing the breathing gas pressure provided to the patient breathing interface;
if the sensed carbon-dioxide level is decreasing, determining if the sensed carbon-dioxide level has crossed a second threshold parameter;
if the sensed carbon-dioxide level has crossed the second threshold parameter, increasing the breathing gas pressure provided to the patient breathing interface; and
the increasing and decreasing of breathing gas pressure maintaining a positive pressure sufficient to sustain open the airway of a patient wearing the breathing interface.

12. The method of claim 11 wherein the step of sensing a carbon-dioxide level associated with a patient breathing interface comprises emitting infrared light within the patient breathing interface.

13. The method of claim 12 wherein the step of sensing a carbon-dioxide level associated with a patient breathing interface comprises detecting infrared light within the patient breathing interface.

14. The method of claim 12 wherein the step of emitting comprising emitting infrared light into a fiber optic cable coupled to the patient breathing interface.

15. The method of claim 14 wherein the step of detecting infrared light comprising sensing the infrared light in a fiber optic cable coupled to the patient breathing interface.

16. The method of claim 11 wherein the step of sensing a carbon-dioxide level associated with a patient breathing interface comprises sensing the carbon-dioxide level vented from the patient breathing interface.

17. The method of claim 11 wherein the step of sensing a carbon-dioxide level associated with a patient breathing interface comprises sensing the carbon-dioxide level using infrared light.

18. A method of providing a breathing gas to a patient comprising the steps of:
sensing a carbon-dioxide level associated with a patient breathing interface;
determining if the sensed level of carbon-dioxide is increasing or decreasing;
if the sensed level of carbon-dioxide is decreasing, determining whether the sensed level of carbon-dioxide at or below a threshold level;
if the sensed level of carbon-dioxide is at or below the threshold level, increasing the pressure of the breathing gas for a fixed period of time;
decreasing the pressure of the breathing gas upon expiration of the fixed period of time;
the increasing and decreasing of the pressure of the breathing gas maintaining a positive pressure sufficient to sustain open the airway of the patient.

19. The method of claim 18 wherein the step of sensing a carbon-dioxide level associated with a patient breathing interface comprises the step of sensing a carbon-dioxide level with infrared light.

20. The method of claim 19 wherein the step of sensing a carbon-dioxide level with infrared light comprises the step of sensing a carbon-dioxide level vented from the patient breathing interface.

21. The method of claim 18 wherein the step of increasing the pressure of the breathing gas for a fixed period of time comprises initiating a monostable timer.

22. The method of claim 18 wherein the step of increasing the pressure of the breathing gas for a fixed period of time comprises initiating a timer.

23. The method of claim 22 wherein the step of decreasing the breathing gas pressure provided to the patient breathing interface after a predetermined period of time comprises decreasing the breathing gas pressure upon expiration of the timer.

24. A method of administering a CPAP therapy comprising the steps of:
monitoring the level of carbon-dioxide vented from a patient breathing interface;
if the level of carbon-dioxide vented is decreasing, determining of the level of carbon-dioxide is at or below a threshold value;
if the level of carbon-dioxide vented is at or below the threshold value, providing a first positive airway pressure to the patient breathing interface for a fixed period of time; and
upon the expiration of the fixed period of time providing a second positive airway pressure to the patient breathing interface.

25. A method of providing a breathable gas by monitoring a carbon dioxide level, comprising:
sensing the carbon dioxide level associated with a breathing interface;
determining if the carbon dioxide level is above or below a threshold value;
if the carbon dioxide level is above the threshold value, decreasing the pressure of the breathable gas; and
if the carbon dioxide level is below the threshold value, increasing the pressure of the breathable gas to maintain a positive pressure sufficient to sustain open the airway of a patient wearing the breathing interface.

26. A system for administering breathing gas to a patient breathing interface comprising:
a blower for providing positive pressure breathing gas;
a controller in circuit communication with the blower;
a sensor in circuit communication with the controller for detecting a level of carbon dioxide associated with the patient breathing interface; and
logic for determining if the carbon dioxide level is above a first threshold value or below a second threshold value and for decreasing the pressure of the breathing gas if the carbon dioxide level is above the first threshold value and for increasing the pressure of the breathing gas if the carbon dioxide level is below the second threshold value to maintain open the airway of a patient.

27. The system of claim 26 wherein the first threshold value and the second threshold value are the same value.

28. The system of claim 26 further comprising a timer having a variable off time period and predetermined on time period.

29. The system of claim 26 wherein the sensor comprises an infrared light emitter and detector.

30. The system of claim 29 further comprising optical fibers coupled to the infrared emitter and detector.

31. The system of claim 29 wherein the infrared emitter and detector are located within a housing accommodating the controller.

32. The system of claim 29 wherein the infrared emitter and detector are located within the patent breathing interface.

33. The system of claim 29 wherein the infrared emitter and detector are located proximate to a vent of the patient breathing interface.

* * * * *

UNITED STATES PATENT AND TRADEMARK OFFICE
CERTIFICATE OF CORRECTION

PATENT NO.       : 6,990,980 B2                                    Page 1 of 1
APPLICATION NO.  : 09/967274
DATED            : January 31, 2006
INVENTOR(S)      : Joseph B. Richey, II It is certified that error appears in the above-identified patent and that said Letters Patent is hereby corrected as shown below:

On the Title Page, Item (56), in the U.S. PATENT DOCUMENTS section, please insert:

| | | |
|---|---|---|
| 4,821,736 | 04/1989 | Watson |
| 5,094,235 | 03/1992 | Westenskow et al. |
| 5,193,544 | 03/1993 | Jaffe |
| 5,332,901 | 07/1994 | Eckless et al. |
| 5,954,050 | 09/1999 | Christopher |
| 6,099,481 | 08/2000 | Daniels et al. |

Signed and Sealed this

Twenty-third Day of October, 2007

JON W. DUDAS
*Director of the United States Patent and Trademark Office*